US006531319B1

(12) United States Patent
Pant et al.

(10) Patent No.: US 6,531,319 B1
(45) Date of Patent: Mar. 11, 2003

(54) METHOD OF DETECTING COLON CANCER

(76) Inventors: Keshab D. Pant, 341 Aurora Dr., Perris, CA (US) 92571; John D. McCracken, 646 Valleyview Dr., Redlands, CA (US) 92373; Omar Fagoaga, 1834 Northwestern Cir., Colton, CA (US) 92324; Wayne Kelln, 25232 Lawton Ave., Loma Linda, CA (US) 92354; Sandra Nehlsen-Cannarella, 652 E. Mariposa Dr., Redlands, CA (US) 92373

( * ) Notice: Subject to any disclaimer, the term of this patent is extended or adjusted under 35 U.S.C. 154(b) by 0 days.

(21) Appl. No.: 09/567,748

(22) Filed: May 10, 2000

(51) Int. Cl.[7] ............................................... G01N 33/48
(52) U.S. Cl. ......................... 436/64; 436/501; 436/536; 435/7.1; 530/412; 530/388.8; 530/389.7; 530/350
(58) Field of Search ..................... 435/7.1, 413, 417, 435/418, 422; 530/412, 388.8, 389.7, 350; 436/64, 501, 536

(56) References Cited

U.S. PATENT DOCUMENTS 4,962,187 A  * 10/1990 Pant ............................ 530/350
5,356,817 A  * 10/1994 Cole ............................ 436/64

OTHER PUBLICATIONS

Kitsukawa Y, et al. Jpn J Surg 1979 Jun.; 9 (2): 102–9.*
Pant KD, et al. Hybridoma 1986 Summer; 5 (2): 129–35.*
Pant KD, et al. Tumour Biol 1984; 5 (5) 243–54.*
Shimano T, et al. Dis Colon Rectum 1987 Aug.; 30 (8): 607–10.*
Fujimoto S, et al. Cell Mol Biol 1979; 25 (3): 153–61.*
Pant KD, et al. Am J Clin Pathol 1986 Jul.; 86 (1): 1–9.*
Sugano K, et al. Jpn J Cancer Res 1989 Dec.; 80 (12): 1156–60.*
Shimano T, et al. Dis Colon Rectum 1987 Aug.; 30 (8): 607–10.*
Pant KD, et al. Dig Dis Sci 2002 Jun.; 47 (6): 1236–40.*
Fujimoto S, et al. Jpn J Surg 1981 Jan.; 11 (1): 27–32.*
Ward, AM, 1985, Tumour Markers, Developmental Oncology, vol. 21, pp. 90–106.*
Tockman, MS, et al, 1992, Considerations in bringing a cancer biomarker to clinical application, Cancer Research, vol. 52, Suppl., pp. 2711s–2718s.*
Yuan, M. "Value of fecal detection of cancer–associated antigens using monoclonal antibodies in the diagnosis of colorectal cancer." *Chung Hua Wai Ko Tsa Chih.* Aug., 1990. pp. 497–500.
Yuan, M. "Detection of cancer–associated antigen in feces of patients with gastric cancer by monoclonal antibodies." *Chung Hua Chung Liu Tsa Chih.* Mar., 1991. pp. 103–105.

* cited by examiner

*Primary Examiner*—Anthony C. Caputa
*Assistant Examiner*—Stephen L. Rawlings
(74) *Attorney, Agent, or Firm*—Knobbe, Martens, Olson & Bear, LLP

(57) ABSTRACT

An immunological assay and kit for colon cancer screening is disclosed. Fecal glycoproteins are extracted from individual samples such that immunogenicity is maintained. The purified fecal glycoproteins are reacted with antibodies to Colon and Ovarian Tumor Antigen (COTA). The mucin antigen COTA is specifically present in colorectal cancer tissue and not in normal colons. The amount of COTA in the fecal sample is determined and used to indicate the presence of colon cancer.

12 Claims, 2 Drawing Sheets

METHOD OF DETECTING COLON CANCER

FIELD OF THE INVENTION

The present invention is directed to a method for detecting colon cancer utilizing an antibody specific for a glycoprotein found in colon cancer cells.

BACKGROUND OF THE INVENTION

Colorectal cancer is among the leading causes of cancer-related morbidity and mortality in industrialized nations. The pathogenesis is related to hereditary influences, modified by the quantity and quality of dietary fat. In 1995, the American Cancer society estimated that 135,000 new cases of colon cancer were diagnosed; 71% were in the colon and 30% were in the rectum. Patients diagnosed at an early stage, prior to lymph-node spread, are potentially cured with surgery. At present, only 41% of patients are diagnosed at an early stage. The remaining cases frequently undergo perioperative radiation and/or chemotherapy to attempt to control the metastatic spread of disease. Ultimately, 50% of patients thought to have undergone curative resections eventually develop recurrent disease. Unfortunately, 55,000 Americans die each year due to recurrent or metastatic colon or rectal cancer. The key to enhanced survival is early diagnosis. Colon and rectal cancers are often silent and slowly progressive. Most patients exhibit symptoms such as rectal bleeding, pain, abdominal distension or weight loss only after the disease is advanced and not surgically curable.

Over the past 25 years, early colorectal cancer detection has been based on the fecal occult blood test (FOBT) performed annually on asymptomatic individuals. Current recommendations adapted by several healthcare organizations, including the American Cancer Society, call for fecal occult blood testing beginning at age 50, repeated annually until such time as the patient would no longer benefit from screening. A positive FOBT leads to colonoscopic examination of the bowel; an expensive and invasive procedure, with a serious complication rate of one per 5,000 examinations. Only 12% of patients with heme positive stool are diagnosed with cancer or large polyps at the time of colonoscopy. Most studies show that FOBT screening does not improve cancer-related mortality or overall survival. Compliance with occult blood testing has been poor; less than 20percent of the population is offered or completes FOBT as recommended. If FOBT is properly done, the patient collects a fecal sample from three consecutive bowel movements. Samples are obtained while the patient adheres to dietary guidelines and avoids medications known to induce occult gastrointestinal bleeding. In reality, physicians frequently fail to instruct patients properly, patients frequently fail to adhere to protocol, and some patients find the task of collecting fecal samples difficult or unpleasant, hence compliance with annual occult blood testing is poor. Compounding the problem of compliance, the sensitivity and specificity of FOBT to detect colon cancer is poor. In eight prospective studies where hemoccult testing was followed by colonoscopy, only 41 of 159 cancers diagnosed were detected by FOBT, yielding a screening sensitivity of 26%. FOBT sensitivity for pre-cancerous polyps was also poor. Poor test specificity leads to unnecessary colonoscopy, adding considerable expense to colon cancer screening. In the University of Minnesota trial, a large prospective hemoccult screening study, test specificity was 90%, and positive predictive value was 2%. Only one colon cancer was found in every 50 test-triggered colonoscopies performed.

New methodology of immunological testing has potential advantages over FOBT including improved sensitivity, specificity and patient compliance. If immunological testing is more sensitive and specific than FOBT, the frequency of testing could be reduced, collection of consecutive samples would be eliminated, dietary and medication schedule modifications would be eliminated, and patient compliance would be enhanced. If colon cancer screening by immunological testing is more specific, the problem of false positive test results leading to unnecessary colonoscopic examination would be reduced leading to cost savings and improved safety. Clearly, there is a long felt need for a simple, accurate, and inexpensive screen for colon cancer.

DESCRIPTION OF THE RELATED ART

Since the goblet cells of colorectal cancers produce glycoprotein mucin(s) that are immunologically distinguishable from normal colonic mucin (Nairn et al. Br. Med. J. 1791–1793, 1962) it is possible to detect their presence in the feces by immunological assay. Springer (Springer Science 1198–1206, 1984) reported that T antigens (Thomsen Friedenreich), and Tn antigens, precursors of MN blood group glycoproteins, are tumor associated antigens. Kurosaka et al (Kurosaka et al J. Biol. Chem. 258: 11594–11598, 1983) isolated several oligosaccharides from a rectal adenocarcinoma and reported that one of the major oligosaccharides was sialylated-Tn or STn (NeuAc$\alpha$2–6Gal NAc$\alpha$1-o-ser/thr). Ovine submaxillary mucin is identical in chemical structure as STn disaccharides. Kjeldsen et al. (Kjeldsen, et al. Cancer Res. 48: 2214–2220, 1988) produced TKH1 and TKH2 monoclonal antibodies that react with ovine submaxillary mucin and demonstrated that both were reactive by immunohistochemistry with adenocarcinoma of human lung, stomach, colon, breast and pancreas, but not with normal human tissue samples. Itzkowitz et al. (Itzkowitz et al. Cancer Res. 260: 8262–8271, 1989) observed expression of all the three Tn, Sialosyl-Tn and T antigens in colon cancers. He proposed that in malignancy incomplete glycolsylation and early sialylation of precursor antigen results in premature termination of the carbohydrate chain. In contrast, Podolsky (Podolsky J. Bio. Chem. 260: 15510–15515, 1985) had isolated 21 oligosaccharides from normal colonic mucin and sialylated-Tn was one of them. The non-reactivity of TKH2 antibody with normal colonic mucosa was explained by the work of Jass et al. (Jass et al. Pathology 26: 418–422, 1994) and later Ogata et al. (Ogata et al. Cancer Res. 55: 1869–1874, 1995) who reported that in the normal colon sialic acid is heavily o-acetylated and is masked, thus antibodies cannot react, while in neoplastic tissue o-acetylation is not extensive, and sialic acid is not masked. Removal of the O-acetyl groups from normal colon tissue by alkaline treatment made them reactive with TKH2 antibody.

Pant et al. did initial studies on Colon-Ovarian tumor antigen (COTA) with polyclonal antibodies produced against mucin extracted from human colon cancer tissue removed at surgery. The polyclonal antibodies were made specific by absorption with lyophilized extracts of normal human colon and other normal human tissues and CEA. The resultant antibody retained immunoreactivity towards colon cancer and mucinous ovarian tumors but did not react with normal colon tissue as seen by immunodiffusion and immunofluorescence testing (Pant et al. Tumor Biol. 5: 243–254, 1984). Furthermore, the absorbed anti-COTA antibodies immunostained several colon cancer tissues and LS174T tumor cells and other colon cancer xenografts but did not stain normal human colon sections (Pant et al. Am J. Clin. Path. 86:1–9, 1986). Pant used COTA isolated from LS174T tumor cells to produce a monoclonal antibody SP-21. This antibody gave identical immunohistochemical staining pattern as observed with absorbed polyclonal anti-COTA antibodies (Pant et al. Hybridoma 5: 129–135, 1986). In an extended immunohistochemical study with SP-21 monoclonal antibody, Dorman et al (Dorman et al. J. Clin. Path. 45: 932–933, 1992) observed that SP-21 immunostained several other human cancer tissues including ovary, stomach, breast, esophagus, prostate, pancreas and endometrium.

The relationship of COTA to STn was established by chemical analysis of purified COTA, blocking of immunoreactivity by N-acetyl neuraminic acid and loss of immunoreactivity after neuraminidase treatment. It was concluded that neuraminic acid is an essential component of COTA (Pant, et al. Journal of Tumor Marker Oncology 3:1–13, 1988). The identity of COTA to STn was further established by comparison of SP-21 with TKH1. Kordari et al. reported neuraminidase treatment and O-glycanase treatments of colon cancer tissue completely destroyed TKH1 and COTA epitope reactivity indicating that TKH 1 and COTA monoclonal antibodies recognized the NeuAcα2–6GalNAc disaccharide exclusively (Kordari, et al. Tumor Biol. Abs., 1990).

SUMMARY OF THE INVENTION

The present disclosure is drawn to a method for extracting glycoproteins from a fecal sample such that immunogenicity is maintained comprising the steps of:
(a) obtaining a fecal sample from an individual;
(b) shaking the fecal sample in a preservative solution;
(c) separating the solution containing the fecal sample to produce a fraction comprising glycoproteins;
(d) precipitating the glycoproteins from the fraction comprising glycoproteins; and
(e) dissolving the precipitated glycoproteins in buffer.

The method may further comprise the steps of:
(f) centrifuging the solution from step (e) to produce a pellet and a supernatant; and
(g) collecting the supernatant containing the extracted glycoproteins.

In a preferred embodiment, the fecal sample is collected in a clean vial containing preservative wherein the preservative comprises ethanol and formalin at a concentration such that bacterial growth is retarded and extraneous fecal matter is precipitated while maintaining immunogenicity of glycoproteins in the fecal sample. Preferably, the preservative comprises 25–45% ethanol with 0.025%–0.35% formalin. More preferably, the preservative comprises 40% ethanol with 0.25% formalin.

In a preferred embodiment, the solution containing the fecal sample is separated by centrifugation. More preferably, the centrifugation is at 1040–1500×g for 10–15 minutes at room temperature.

In a preferred embodiment, the glycoproteins are precipitated from the fraction comprising glycoproteins with 3 volumes of 100% ethanol with 0.1 ml of 20% sodium acetate. More preferably, the, precipitation proceeds for about 3 hours at room temperature. Preferably, the precipitated glycoproteins are dissolved in phosphate buffered saline.

The present disclosure is also drawn to a method for screening for colon cancer comprising:
(a) obtaining purified fecal glycoproteins, said glycoproteins being obtained by a method comprising:
(i) obtaining a fecal sample from an individual;
(ii) shaking the fecal sample in a preservative solution;
(iii) separating the solution containing the fecal sample to produce a fraction comprising glycoproteins;
(iv) precipitating the glycoproteins from the fraction comprising glycoproteins; and
(v) dissolving the precipitated glycoproteins in buffer; and
(b) determining the level of COTA antigen in the purified fecal glycoproteins.

In a preferred embodiment, the fecal sample is collected in a clean vial containing preservative wherein the preservative comprises ethanol and formalin at a concentration such that bacterial growth is retarded and extraneous fecal matter is precipitated while maintaining immunogenicity of glycoproteins in the fecal sample. Preferably, the preservative comprises 25–45% ethanol with 0.025%–0.35% formalin. More preferably, the preservative comprises 40% ethanol with 0.25% formalin.

In a preferred embodiment, the solution containing the fecal sample is separated by centrifugation. More preferably, the centrifugation is at 1040–1500×g for 10–15 minutes at room temperature.

In a preferred embodiment, the glycoproteins are precipitated from the fraction comprising glycoproteins with 3 volumes of 100% ethanol with 0.1 ml of 20% sodium acetate. More preferably, the precipitation proceeds for about 3 hours at room temperature. Preferably, the precipitated glycoproteins are dissolved in phosphate buffered saline.

In a preferred embodiment, the determination of the level of COTA antigen in the purified glycoproteins comprises the steps of:
(a) reacting an antibody for COTA antigen with the extracted glycoproteins to form a complex of the antibody and the COTA antigen;
(b) exposing the complex to a second antibody, wherein said second antibody is a detection agent; and
(c) determining the level of the detection agent and in turn determining the presence of COTA antigen in the fecal sample.

In one embodiment, the antibody for COTA antigen is bound to a solid surface. In an alternate embodiment, the extracted glycoproteins are bound to a solid surface. Preferably, the antibody for COTA antigen is monoclonal antibody SP-21.

The present disclosure is also drawn to a kit for screening for colon cancer comprising:

an anti-COTA capture antibody bound to a solid support;

purified human COTA antigen; and a vial containing a preservative solution.

In one embodiment, the solid support is an ELISA plate. In an alternate embodiment, the solid support is a membrane filter. In a preferred embodiment, the kit contains the monoclonal antibody SP-21 as the antibody for COTA antigen.

In a preferred embodiment, the kit contains a preservative solution which comprises 25–45% ethanol with 0.025%–0.35% formalin. In a most preferred embodiment, the kit contains a preservative comprising 40% ethanol with 0.25% formalin.

DETAILED DESCRIPTION OF THE PREFERRED EMBODIMENT

Figure 1:
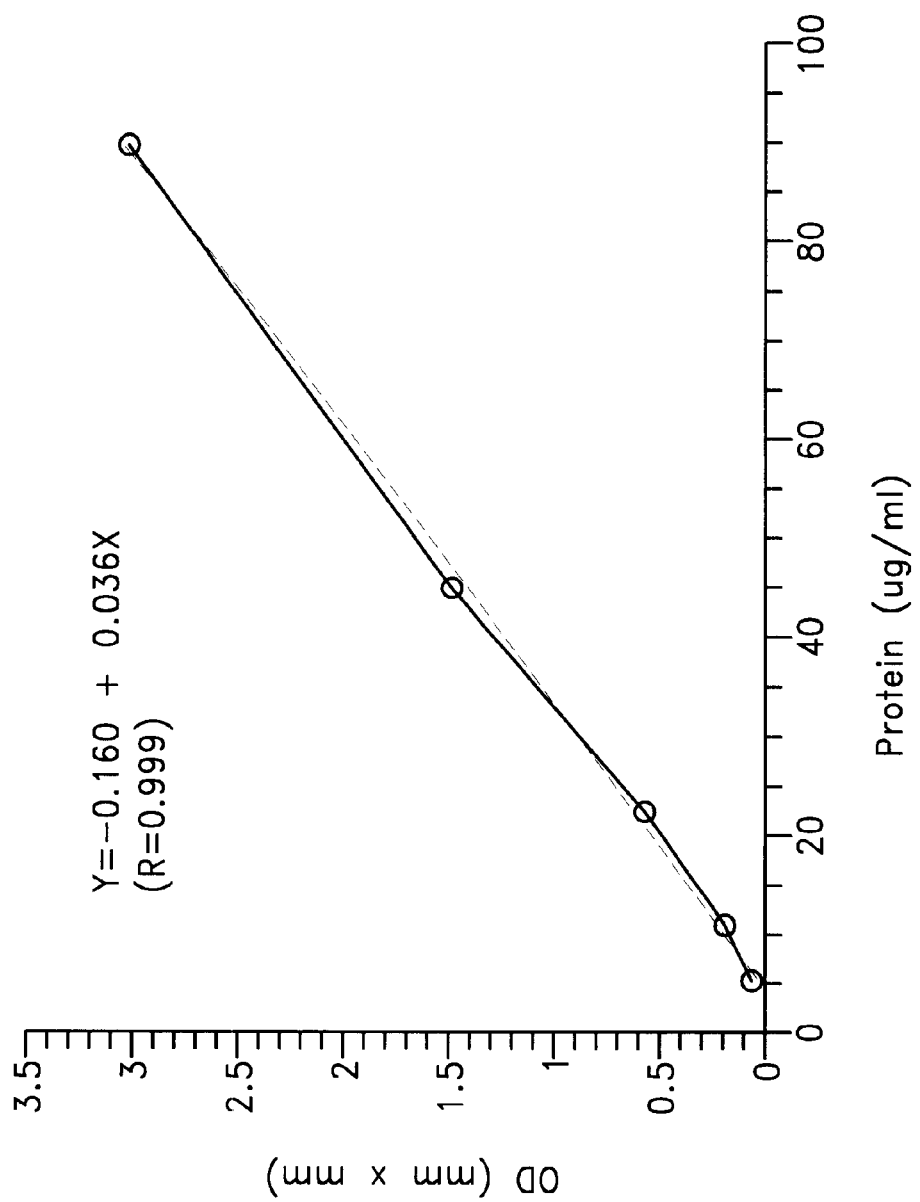
FIG. 1. Plot of optical density of slot-dots obtained on dilutions of purified COTA protein from LS 174T.

The hemocult test is based on pseudoperoxidase activity of heme which oxidizes gum guaiac to a blue color. It is well recognized that the test also detects presence of blood in the digestive tract from sources other than colorectal cancers or adenomas. Furthermore, the peroxidase activity is also present in some foods. Certain chemicals which inhibit the pseudoperoxidase emzyme activity can yield false negative results affecting the sensitivity and specificity of the test.

The present disclosure relates to an immunological assay method and kit to apply to population-based colon cancer screening which avoids problems associated with the hemocult test discussed above.

In a preferred embodiment, the fecal sample is obtained using a commercially available stool collection device such as one available from Ability Building Center, Rochester, Minn., and is then placed immediately in a preservative solution so as to inhibit bacterial multiplication and sample glycoprotein degradation. Glycoproteins are then isolated from the fecal sample at a later time. The preservative solution contains ethanol and formalin at a concentration such that bacterial growth is retarded and extraneous fecal matter is precipitated while maintaining immunogenicity of glycoproteins in the fecal sample. Extraneous fecal matter includes components other than the glycoprotein fraction. Preferably, the preservative solution contains 0.025%–0.35% formalin in 25–45% ethanol. In a preferred embodiment, the preservative contains 40% ethanol with 0.25% formalin to optimally prevent bacterial multiplication and glycoprotein degradation without loss of glycoprotein immunoreactivity.

A key feature of the presently claimed invention is the extraction of the desired glycoproteins from the preservative solution while maintaining immunogenicity. Any method for extraction of glycoproteins which maintains immunogenicity of the extracted mucins may be used in the screening method. In general, the fecal sample in the preservative solution is separated to obtain a fraction containing the glycoproteins. Any means known to those skilled in the art may be used to fractionate the fecal sample including, but not limited to centrifugation, filtration, and chromatography. In a preferred embodiment, centrifugation is used to isolate the glycoprotein-containing fraction, preferably at 1040×g to 1500×g for 10–15 min. Most preferably, centrifugation at 1040×g for 10 minutes at room temperature is used to obtain a supernatant containing glycoproteins. The glycoprotein-containing fraction is then further purified by precipitation of the glycoproteins including COTA. Means to precipitate the glycoproteins include, but are not limited to, precipitation with ammonium sulfate, or organic solvents, such as ethanol and acetone, or a combination thereof. Alternatively, the glycoproteins may be further purified by means known to those skilled in the art such as column chromatography, gel filtration and the like. In a preferred embodiment the glycoprotein-containing fraction is precipitated with ethanol and sodium acetate and then centrifuged to obtain a precipitate. The precipitated pellet is resuspended in buffer and recentrifuged to obtain a supernatant containing the glycoproteins to be screened, preferably at 1500×g to 2040×g for 15–20 minutes. In a preferred embodiment, the resuspended pellet is centrifuged at 1500×g for 15 minutes.

The level of COTA antigen in the supernatant containing the glycoproteins is then determined. The mucin antigen COTA is specifically present in colorectal cancer tissue and not in normal colon tissue. Since COTA mucin is produced by goblet cells and eventually gets mixed with the feces, detection and estimation of it in the fecal samples is the basis of the present non-invasive test for colorectal cancer.

Any antibody which binds to Colon and Ovarian Tumor Antigen (COTA) may be used for quantitation of COTA levels as a colon cancer screen. A representative monoclonal antibody includes SP-21. A monoclonal antibody which binds to COTA may be obtained by isolation of COTA from the LS174T cell line (ATCC CL-188) using well known methods (Kohler and Milstein (1975) Nature 256: 495–497, for example). The antibody for COTA antigen is reacted with the extracted glycoproteins to form a complex of the antibody and the COTA antigen. In a preferred embodiment, a combination of one IgG antibody and one IgM antibody is used. Any means available for facilitation of antibody-antigen binding may be used in the disclosed method including but not limited to tubes, filters, beads, multiwell plates and a mixture thereof. Preferred embodiments use either ELISA plate technology or slot dot assays. Means to quantitate the extent of binding include detection using colorimetric assays as well as radioimmunoassay. In a preferred embodiment, the complex of the antibody and the COTA antigen is exposed to a second antibody which is labelled such that the level of COTA antigen in the glycoprotein sample may be detected and quantitated by reference to a standard curve prepared from dilutions of purified COTA. Such labels include, but are not limited to, radioactive and colorimetric methods including absorption, bioluminescence and fluorescence labeling means. In a preferred embodiment, the second antibody is biotinylated and is subsequently treated with peroxidase conjugated streptavidin to produce a quantifiable colorimetric signal. Levels of COTA antigen detected by the Dot assay greater than 15 $\mu$g/ml predict the presence of colon cancer with sensitivity of 83% and specificity of 96%. ELISA methodology may also be used to detect COTA antigen. A cut off value for detection of colon cancer in $\mu$g/ml will be based upon values obtained from normal individuals.

The invention is further set forth in the following examples, which are in no way intended as a limitation upon the scope of the invention.

EXAMPLES

A more detailed description of the present invention is provided below. While the described embodiment represents the preferred embodiment of the present invention, it is to be understood that modifications will occur to those skilled in the art without departing from the spirit of the invention. The scope of the invention is therefore to be determined solely by the appended claims.

Example 1
Patient Selection and Sample Collection

One hundred patients with risk factors or signs of colon cancer scheduled for colonoscopic examination were contacted. Indications for colonoscopy included hemoccult positive stools, rectal bleeding, prior history of adenoma or colon cancer, or family history of colon cancer. A kit containing a vial with 20 ml of preservative (40% ethanol with 0.25% formalin solution) and a fecal collection device were mailed to the patient. Patients were asked to collect approximately 1–2 gm of feces and place it into the vial. The kit was returned on the day of their colonoscopy.

Extraction of Glycoproteins From Fecal Samples

The contents of the vial were shaken vigorously to mix the fecal sample completely and then centrifuged at 1040×g for 10 minutes at room temperature (RT) to remove solid fecal debris and the clear supernatant was collected. 3 volumes of 100% ethanol with 0.1 ml of 20% sodium acetate was added to the supernatant containing the glycoprotein fraction. Precipitation proceeded for 3 hours at room temperature. The precipitate was collected by centrifugation at 1040×g for 10 minutes. Traces of ethanol from the precipitate were removed by aeration. The precipitate was dissolved in 1 ml of Phosphate Buffered Saline (PBS). The preparation was further centrifuged at 1500×g for 15 minutes and the clear supernatant was collected.

Protein Quantitation

Protein quantitation of the samples was done by Pierce Bicinchoninic reagent. The assay contained (a) 100 μl each of doubling dilutions of bovine serum albumin (BioRad) ranging from 745 μg/ml, 372 μg/ml, 186 μg/ml, 93 μg/ml and 46.5 μg/ml for obtaining a standard curve; (b) 100 μl of a sample of purified COTA; and (c) 100 μl of PBS as negative control. 2 ml of complete BCA reagent was added and tubes were covered and incubated at RT for 2 hours. O.D. of the sample was taken at 562 nm in a SHIMADZU UV-160 spectrophotometer. All patient samples were diluted and normalized to 60 μg/ml protein concentration. Alternatively, protein concentrations can be obtained by spectrophotometry by adding 1 ml of sample to a quartz cuvette and measuring absorbance at 280 nm.

Standard Curve of COTA

Highly purified COTA was prepared from LS174T tumors (ATCC #CL-188) by Westphals hot phenol method for complex carbohydrates (Westphal et al. Zeitschrift Fur Naturforschung 76: 148–155, 1952). Briefly, the mucinous tumor was treated with equal volume of phenol and heated at 65 C for 30 minutes. After cooling and centrifugation, the upper water soluble fraction was separated and precipitated with 3 volumes of ethanol. The precipitate was dissolved in PBS, pH 7.4, dialysed and recentrifuged. It was fractionated on a Sepharose-4B column and the fractions containing COTA reactivity were pooled and concentrated. The preparation contained very low protein and had high COTA reactivity. Two-fold dilutions of COTA ranging in protein values of 90 μg/ml, 45 μg/ml, 22.5 μg/ml, 11.2 μg/ml and 5.6 μg/ml were used in the dot assay and in preparation of the standard curve.

Colonoscopy

Patients were prepped for diagnostic colonoscopy by adhering to a clear liquid diet the day prior to exam, and taking an oral bowel preparation (COLYTE) the night prior to exam. Patients underwent colonoscopy, the gold standard diagnostic test for colorectal neoplasia, with OLYMPUS or PENTAX video endoscopy, by board-certified gastroenterologists appointed to the GI laboratories of Loma Linda University Medical Center or Loma Linda Veterans Administration Medical Center. Diagnostic information, including the size and location of any neoplastic lesion was recorded in the procedure note, which in-turn was forwarded to the GI research laboratory for data acquisition. The written pathology report was obtained from the pathology Department, LLUMC or LLVAMC, and information was abstracted regarding tumor stage. If the patient underwent surgical resection, the operative report and final pathology report were reviewed to obtain tumor stage.

Slot-Dot Assay of Samples and of Dilutions of Purified COTA 0.2 μm PROTAN nitrocellulose membrane (Schleicher and Schuell) was placed in a Bio-Rad slot-dot apparatus. 20 μl of each test sample, known positive and negative control samples, and doubling dilutions of purified COTA and PBS were applied in the slots. The samples were allowed to bind to the membrane for 30 minutes. The membrane was then blocked with 3% non-fat milk for 30 minutes. The membrane was washed with PBS three times and then reacted with 1 μg/ml of monoclonal SP-21 antibody for 60 minutes in a humid chamber at RT. The nitrocellulose strip was then washed with PBS and reacted with 1:2 diluted biotinylated goat anti-mouse antibody (DAKO LSAB2 kit) and incubated for 15 minutes at RT in a humid chamber. After washing three times with PBS, the membrane was reacted with peroxidase conjugated streptavidin (DAKO LSAB2) for 10 minutes at RT in a humid chamber. The membrane was washed three times with PBS and then reacted with a solution of 5 mg/10 ml of 3,3' diaminobenzidine tetrahydrorhloride made in Tris buffer, pH 7.2 with 0.01% $H_2O_2$ for 90 seconds. The membrane was washed with running tap water and allowed to dry. The intensity of the slot-dot color was quantitated by reflectance reading in a Bio-Rad model GS-700 imaging densitometer and computer generated O.D. values were obtained. A standard curve was drawn by plotting the COTA protein versus the optical density values. From this curve, corresponding COTA equivalent protein vamounts of the samples were calculated. Samples showing protein amounts greater than 15 μg/ml for COTA were interpreted as positive.

Example 2

Screening for Detection of Colon Cancer Using Slot Blot Assay

Figure 2:
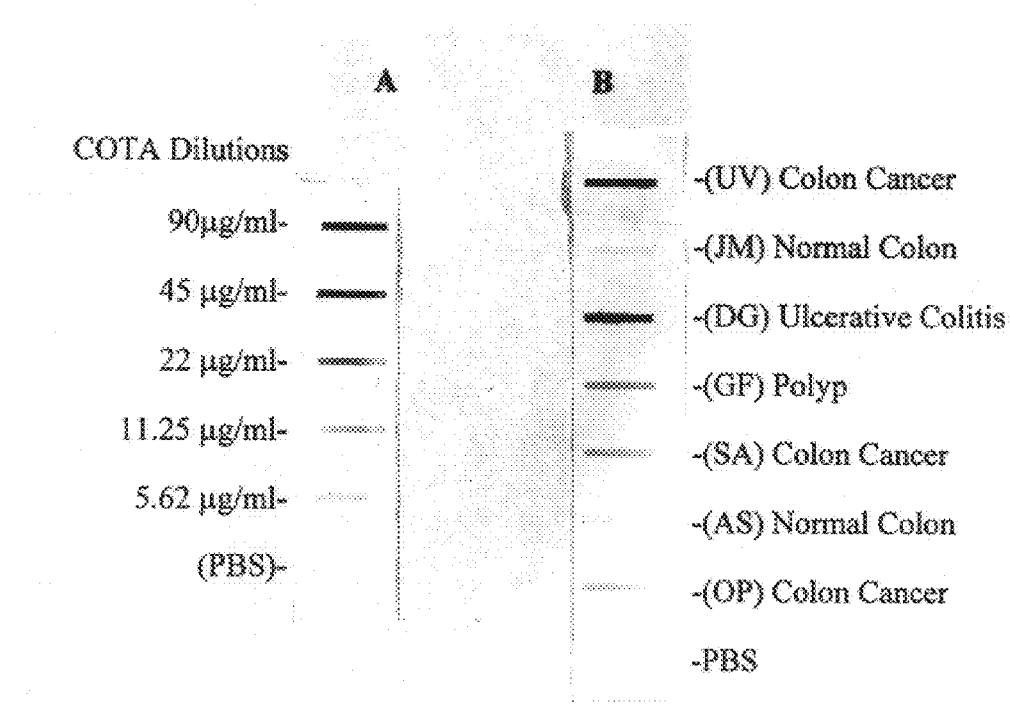
FIG. 2. Lane A. Graded intensity of slot-dots of purified COTA dilutions. Lane B. Slot-dots of 3 patients with colon cancer, 1 with ulcerative colitis and dysplasia, 1 with polyp, 3 normal individuals and control PBS.

On application of 20 μl of doubling dilutions of 90 μg/ml of purified COTA in slot-dot assay, a graduation in color intensity was obtained (FIG. 2, lane A). Plotting the densitometer reading of each slot-dot of purified COTA dilution against the protein amount (Table 1) resulted in a curve with 99.8% coefficient of correlation (FIG. 1). Samples with O.D. value exceeding 0.45 (15 μg/ml COTA protein) were considered positive. Positive slot-dots on 3 colon cancer patients, 1 ulcerative colitis and 1 polyp and negative slot-dots on 2 normal colon extracts and PBS with values lower than 15 μg/ml are seen in FIG. 2, lane B.

TABLE 1

Densitometer readings of slot-dots of purified COTA

| COTA protein (μg/ml) | Adjusted volume O.D. (mm × mm) |
| --- | --- |
| 90 | 3.09 |
| 45 | 1.56 |
| 22.5 | 0.61 |
| 11.2 | 0.21 |
| 5.6 | 0.074 |

Sample kits were sent to 123 patients scheduled for colonoscopic examination. 94 patients returned the sample for analysis (76.4%). Examination of 100 fecal samples for COTA levels (Table 2) consisted of 94 individuals who were examined by colonoscopy and 6 healthy volunteers who did not have colonoscopy. Of the 6 patients diagnosed with colon cancer, 5 had COTA levels higher than 15 μg/ml thus resulting in 83.3% positivity. The mean COTA value of 6 colon cancer patients was 20.8 μg/ml and the mean value of 58 normal patients was 7 μg/ml. These results indicate 83.3% sensitivity and 96.5% specificity of the test. Of the 6 patients who had prior colorectal cancers, 4 had resection of the tumors and 2 had radiation treatment of rectal cancer. Of these with previously treated colon cancer, one patient was positive but had 6 mm sessile polyp and had colonic obstruction at the time the fecal COTA test was performed. Of 22 cases of polyps with polyp size ranging from 2 mm to 25 mm, 6 had values over 15 μg/ml thus resulting in 27.2% positivity. Of 8 ulcerative colitis cases tested, one patient was strongly positive. Colonoscopy with biopsy on this patient revealed high grade dysplasia. The group of normal patients included 6 healthy normal volunteers. Of the remaining 52 patients who had colonoscopy done, findings include: 21 normal, 26 with diverticulosis, 4 with hemorrhoids and one with anal fissure. A single case of hemorrhoids and anal fissure gave values in the positive range thus resulting in 3.44% positivity. These results indicate that large percentage of patients with colorectal cancer can be detected when screened for COTA in their feces.

It may be of interest to periodically follow the patients who had earlier radiation treatment or surgery or had polyps and were strongly positive for COTA. It is of significance that one of the ulcerative colitis patients who had very high amounts of COTA in the feces was also diagnosed with high grade dysplasia (see Table 2, below). Among individuals who had normal colonoscopy, only 3.4% had COTA levels higher than 15.0 $\mu$g/ml. This indicates specificity and suitability of the test for screening colorectal neoplasms.

TABLE 2

Patient samples showing COTA values of 15 $\mu$g/ml or higher as positives

| Patients | No. tested | No. positive | No. negative | % positive |
|---|---|---|---|---|
| Colorectal CA | 6 | 5 | 1 | 83.3 |
| Colorectal CA (Resected or radiation treated) | 6 | 1 | 5 | 16.6 |
| Polyps | 22 | 6 | 16 | 27.2 |
| Ulcerative colitis | 7 | 0 | 7 | 0 |
| Ulcerative colitis with dysplasia | 1 | 1 | 0 | 100 |
| Normals | 58 | 2 | 56 | 3.4 |

Example 3
Hybridoma Production

Monoclonal anti-COTA producing hybridomas were generated by immunization of Balb/cj mice with highly purified COTA followed by fusion of splenocytes with SP2/0 myeloma cells. Hybridoma fluids of IgG isotype clones 13B5, 9B4, 15C11 and 15H11 and IgM isotype clones 2C3, 3G4 and IBH2 have shown immunoreactivity towards COTA. The monoclonal antibodies 13B5 (IgG) and 2C3 (IgM) will be further purified by column chromatography and protein A binding. Other monoclonal antibodies of hybridomas (9B4 and 15C11 or 15H11) produced in our laboratory and not yet tested will be analyzed to determine if ELISA system sensitivity and specificity can be enhanced.

Example 4
ELISA Assay for the Detection of COTA

ELISA for quantification of COTA in stool extracts will be developed. The ELISA will be validated for crude stool extracts and purified stool fractions. Twenty-four samples (in duplicate) can be processed in a single ELISA plate. Details of ELISA plate development are as follows:

13B5 (IgG) (or alternate antibody) will be bound in the wells of a microtiter plate as the "capture" antibody. Patient fecal samples appropriately purified and diluted as described above will be added to the wells. If COTA is present in the fecal sample, it is immobilized by binding to the capture antibody. Bound COTA is then detected by the addition of horseradish peroxidase conjugated monoclonal antibody 2C3 (IgM) (or alternate antibody), and subsequent addition of O-phenylenediamine-$H_2O_2$ made in citrate buffer and taking the O.D. of the color reaction at 492 nm. The amount of COTA in each sample is determined by comparison with a standard curve of COTA protein serial dilutions.

For each ELISA test plate, positive standards will include ovine submaxillary mucin and purified human COTA antigen in sufficient quantity as part of the ELISA kit. The standards developed will be tested in a protein matrix similar to the final sample preparation provided in the kit. Alternate ELISA configuration will be formulated and tested. This will include binding of COTA antigen directly to the ELISA 96-well plate and detecting its presence by 13B5 (IgG) and 2C3 (IgM) monoclonal antibodies. To test this procedure, additional clones IgG isotypes 9B4, 15C11 and 15H11 and IgM isotypes 3G4 and 18H2 with known reactivity to COTA will be grown in hybridoma growth tissue culture medium and subsequently purified by liquid chromatography.

Antibody Binding to the Plate and Blocking the Reactive Sites

100 $\mu$l of the capture antibody diluted in binding buffer to 10 $\mu$g/ml is added to each well. The plate is then washed 3×with Tris buffered saline, pH 7.6, and then blocked by adding 200 $\mu$l of SUPERBLOCK to each well. The washing procedure is repeated two more times. The microtiter plate is used immediately in ELISA test or alternatively air dried at room temperature. The dried plates are then sealed in a ziplock plastic bag containing desiccant and stored up to 12 months at 4C.

Antigen Bound to Plates for Testing the Presence of COTA or for Testing Hybridoma Fluids Wash plate 3 times with previously bound antigen and then block the remaining sites with 300 $\mu$l of blocking buffer and incubate for 30 min. The plate is then washed 3 times in wash buffer. 100 $\mu$l of the first antibody or test antibody is diluted to proper concentration in carrier buffer and added to blanks, positive and controls (Hybridoma fluids not to be diluted in carrier buffer). The plates are incubated for 60 min. at room temperature and then washed 3 times with wash buffer. 100 $\mu$l of second antibody diluted in carrier buffer is added to each well and incubated for 60 min. The plate is then washed 3 times with wash buffer. Then 100 $\mu$l of proper substrate is added to each well and the plate is incubated for 30–60 min. at room temperature. The absorbance is then read using a plate reader with wavelength set according to type of enzyme-linked second antibody and substrate used.

Data Analysis

COTA levels expressed in micrograms per ml stool sample will be determined by ELISA. Levels will be correlated with the clinical grade and stage of any neoplasm present, i.e. pre-cancerous polyp, non-invasive or invasive colon cancer, and with the disease location, i.e.: rectosigmoid, descending, transverse or ascending colon. Test sensitivity and specificity will be determined for disease stage and location. The positive predictive value of the COTA immunology test compared with paired hemocult testing will be reported.

What is claimed is:

1. A method for screening for colon cancer in an individual comprising:
   (a) obtaining purified fecal glycoproteins, said glycoproteins being obtained by a method comprising:
      (i) obtaining a fecal sample for the individual;
      (ii) shaking the fecal sample in a preservative solution;
      (iii) separating the solution containing the fecal sample to produce a fraction comprising glycoproteins;
      (iv) precipitating the glycoproteins from the fraction comprising glycoproteins; and
      (v) dissolving the precipitated glycoproteins in buffer; and (b) determining the level of COTA antigen in the purified fecal glycoproteins from the fecal sample, thereby screening for colon cancer in the individual.

2. The method of claim 1 wherein the fecal sample is collected in a clean vial containing preservative wherein the preservative comprises ethanol and formalin at a concentration such that bacterial growth is retarded and extraneous fecal matter is precipitated while maintaining immunogenicity of glycoproteins in the fecal sample.

3. The method of claim 2 wherein the preservative comprises 25–45% ethanol with 0.025%–0.35% formalin.

4. The method of claim 3 wherein the preservative comprises 40% ethanol with 0.25.% formalin.

5. The method of claim 1 wherein the solution containing the fecal sample is separated by centrifugation.

6. The method of claim 5 wherein centrifugation is at 1040–1500×g for 10–15 minutes at room temperature.

7. The method of claim 1 wherein the glycoproteins are precipitated from the fraction comprising glycoproteins with 3 volumes of 100% ethanol with 0.1 ml of 20% sodium acetate.

8. The method of claim 7 wherein the precipitation proceeds for about 3 hours at room temperature.

9. The method of claim 1 wherein the precipitated glycoproteins are dissolved in phosphate buffered saline.

10. A method according to claim 1 wherein determination of the level of COTA antigen in the purified glycoproteins comprises the steps of:
   (a) reacting an antibody for COTA antigen with the purified fecal glycoproteins to form a complex of the antibody and the COTA antigen;
   (b) exposing the complex to a second antibody, wherein said second antibody is a detection agent; and
   (c) determining the level of the detection agent and in turn determining the presence of COTA antigen in the fecal sample.

11. The method of claim 10 wherein the antibody for COTA antigen is bound to a solid surface.

12. The method of claim 10 wherein the extracted glycoproteins are bound to a solid surface.

* * * * *